United States Patent [19]

Kranz et al.

[11] Patent Number: 5,076,833
[45] Date of Patent: Dec. 31, 1991

[54] HERBICIDAL AND PLANT GROWTH-REGULATING 6-(PENT-3-YL)-1,2,4-TRIAZIN-5(4H)-ONES

[75] Inventors: Eckart Kranz, Wuppertal; Karl-Julius Reubke, Cologne; Klaus Lürssen, Bergisch-Gladbach; Hans-Joachim Santel, Leverkusen; Robert R. Schmidt; Birgit Krauskopf, both of Bergisch-Gladbach, all of Fed. Rep. of Germany

[73] Assignee: Bayer Aktiengesellschaft, Leverkusen, Fed. Rep. of Germany

[21] Appl. No.: 517,262

[22] Filed: May 1, 1990

[30] Foreign Application Priority Data

May 25, 1989 [DE] Fed. Rep. of Germany ....... 3917044

[51] Int. Cl.$^5$ .................. C07D 253/07; A01N 43/707
[52] U.S. Cl. .......................................... 71/93; 544/182
[58] Field of Search .................... 544/182; 71/93

[56] References Cited

U.S. PATENT DOCUMENTS

| 3,671,523 | 6/1972 | Westphal et al. | 544/182 |
|---|---|---|---|
| 3,905,801 | 9/1975 | Fawzi | 71/93 |
| 3,961,936 | 6/1976 | Westphal et al. | 71/93 |
| 3,966,715 | 6/1976 | Westphal et al. | 544/182 |
| 4,057,417 | 11/1977 | Dickore et al. | 544/182 |
| 4,346,220 | 8/1982 | Fawzi | 71/93 |
| 4,544,744 | 10/1985 | Schmidt | 544/182 |

FOREIGN PATENT DOCUMENTS 0144668 6/1985 European Pat. Off. .
0150677 8/1985 European Pat. Off. .

Primary Examiner—John M. Ford
Attorney, Agent, or Firm—Sprung Horn Kramer & Woods

[57] ABSTRACT

A herbicidal or plant growth-regulating 6-(pent-3-yl)-1,2,4-triazin-5(4H)-one of the formula

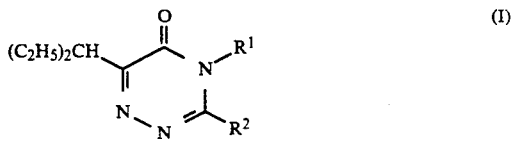

in which
R$^1$ represents amino and
R$^2$ represents alkylthio having more than 1 carbon atom, alkylamino or dialkylamino,
or
R$^1$ represents methylamino and
R$^2$ represents alkylthio.

6 Claims, No Drawings

HERBICIDAL AND PLANT GROWTH-REGULATING 6-(PENT-3-YL)-1,2,4-TRIAZIN-5(4H)-ONES

The present invention relates to new 6-(pent-3-yl)-1,2,4-triazin-5(4H)-ones, to several processes for their preparation, and to their use as herbicides and plant growth regulators.

It has already been disclosed that certain 6-secpentyl-1,2,4-triazin-5(4H)-ones, such as, for example, 4-amino-3-methylthio-6-(pent-3-yl)-1,2,4-triazin-5(4H)-one, have herbicidal properties, U.S. Pat. No. 4,544,744 issued Oct. 1, 1985.

Furthermore, various substituted 6-alkyl-3,4-diamino-1,2,4-triazin-5-(4H)-ones and their herbicidal and insecticidal properties have been described (cf. EP-A 0,150,677).

In addition, it is already known that symmetrical triazine derivatives, such as, for example, 2-chloro-4-ethylamino-6-isopropylamino-1,3,5-triazine (atrazine) have herbicidal properties (cf. R. Wegler, Chemie der Pflanzenschutz- und Schadlingsbekampfungsmittel, [Chemistry of Plant Protection Agents and Pesticides], Vol. 2, p. 368, Springer Verlag, 1970).

However, the herbicidal activity of these pre-viously known compounds against problem weeds, as well as their tolerance by certain crop plants, is not entirely satisfactory in all fields of application.

The new 6-(pent-3-yl)-1,2,4-triazin-5(4H)-ones of the formula (I)

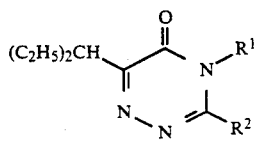

in which
R$^1$ represents amino and
R$^2$ represents alkylthio with more than 1 carbon atom, alkylamino or dialkylamino,
or
R$^1$ represents methylamino and
R$^2$ represents alkylthio,
have been found.

Moreover, it has been found that the new 6-(pent-3-yl)-1,2,4-triazin-5(4H)-ones of the formula (I) are obtained when (a) 4-amino-3-mercapto-6-(pent-3-yl)-1,2,4-triazin-5(4H)-one, of the formula (II),

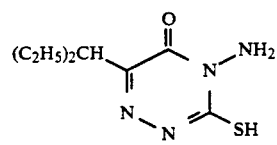

is reacted in an alkaline solution with an alkyl halide, preferably alkyl iodide or alkyl bromide, and, if appropriate, (b) the 3-alkylthio-4-amino-6-(pent-3-yl)-1,2,4-triazin 5(4H)-one obtained in process (a), of the formula (Ia)

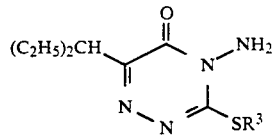

in which
R$^3$ represents alkyl, preferably having 1 to 4 carbon atoms,
is reacted in a two-phase system with a methylating agent in the presence of a phase transfer catalyst, or (c) the 3-alkylthio-4-amino-6-(pent-3-yl)-1,2,4-triazin-5(4H)-one obtained in process (a), of the formula (Ia)

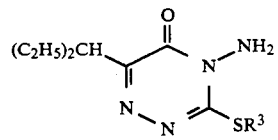

in which
R$^3$ represents alkyl, preferably having 1 to 4 carbon atoms,
is reacted with amines of the formula (III)

$$HNR^4R^5 \qquad (III)$$

in which
R$^4$ represents hydrogen or alkyl, preferably having 1 to 4 carbon atoms, and
R$^5$ represents alkyl, preferably having 1 to 4 carbon atoms,
if appropriate in the presence of a diluent and if appropriate in the presence of a lower aliphatic carboxylic acid.

Finally, it has been found that the new 6-(pent-3-yl)-1,2,4-triazin-5(4H)-ones of the formula I) have herbicidal, in particular selectively herbicidal, and plant growth-regulating properties.

Surprisingly, the 6-(pent-3-yl)-1,2,4-triazin-5(4H)-ones of the formula (I) according to the invention show a better herbicidal activity against important problem weeds in comparison with, for example, 2-chloro-4-ethylamino-6-isopropylamino-1,3,5-triazine, which is a similar compound chemically and from the point of its action, while being equally well tolerated by important crop plants, such as, in particular, wheat, barley, corn, soya bean and cotton. Moreover, the compounds of the formula (I) according to the invention additionally show a plant growth-regulating action.

Formula (I) provides a general definition of the 6-(pent-3-yl)-1,2,4-triazin-5(4H)-ones according to the invention. In this formula,
R$^1$ preferably represents amino and
R$^2$ preferably represents straight-chain or branched alkylthio having 2 to 4 carbon atoms, or represents straight-chain or branched alkylamino having 1 to 4 carbon atoms, or represents straight-chain or branched dialkylamino having 1 to 4 carbon atoms in each alkyl moiety;
or
R$^1$ preferably represents methylamino and
R$^2$ preferably represents straight-chain or branched alkylthio having 1 to 4 carbon atoms.

Particularly preferred compounds of the formula (I) are those in which $R^1$ represents amino and $R^2$ represents ethyl- or propylthio; or represents methyl-, ethyl-, propyl- or butylamino; or represents dimethyl-, diethyl- or ethylmethylamino; or $R^1$ represents methylamino and $R^2$ represents methyl-, ethyl- or propylthio.

If, for example, 4-amino-3-mercapto-6-(pent-3-yl)-1,2,4-triazin-5(4H)-one and ethyl iodide are used as the starting substances, the course of the reaction of the process (a) according to the invention may be represented by the following equation:

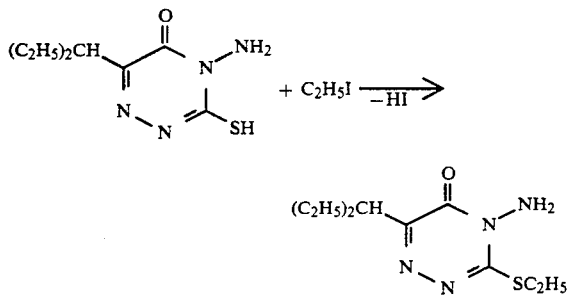

If, for example, 4-amino-3-methylthio-6-(pent-3-yl)-1,2,4-triazin-5(4H)-one and methyl iodide are used as the starting substances, tetrabutylammonium bromide as the phase transfer catalyst and aqueous sodium hydroxide solution/toluene as the two-phase system, the course of the reaction of process (b) according to the invention may be represented by the following equation:

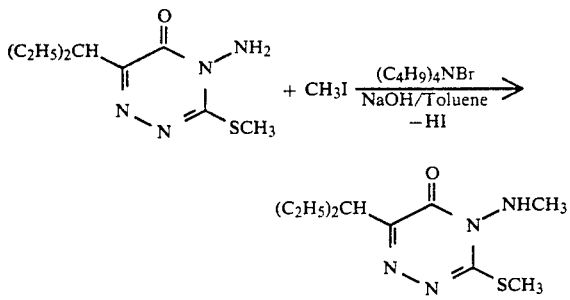

If, for example, 4-amino-3-methylthio-6-(pent-3-yl)-1,2,4-triazin-5(4H)-one and methyl iodide are used as the starting substances, the course of the reaction of process (c) according to the invention may represented by the following equation:

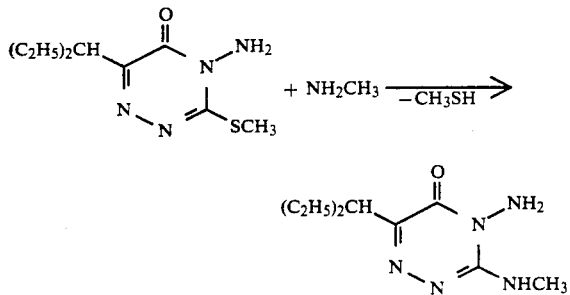

4-Amino-3-mercapto-6-(pent-3-yl)-1,2,4-triazin-5(4H)-one of the formula (II), which is required as starting substance for carrying out process (a) according to the invention, as well as its preparation have already been described (compare U.S. Pat. No. 4,544,744 issued Oct. 1, 1985 and the Preparation Examples).

Preferred methylating agents which are suitable for process (b) according to the invention are methyl iodide, methyl bromide or dimethyl sulphate.

The amines of the formula (III) which are required as starting substances for carrying out process (c) according to the invention are generally known compounds of organic chemistry.

Process (a) according to the invention is carried out in the presence of a base. Bases which are preferably employed in this connection are alkali metal hydroxides, such as sodium hydroxide, in aqueous solution, or alkali metal alkoxides, such as sodium methoxide, with excess alcohol being used as the solvent.

When carrying out process (a) according to the invention, reaction temperatures can be varied within a substantial range. In general, the process is carried out between 0° C. and 100° C., preferably between 0° C. and 50° C.

When carrying out process (a) according to the invention, it is preferred to employ 1 to 1.5 mols of alkylating agent per mol of the compound of the formula II). The intermediates or end products of the formula (Ia) are isolated in a customary manner.

Process (b) according to the invention is carried out in a two-phase system, preferably using an organic solvent which is not miscible with water, and an aqueous solution of a strong base and of a phase transfer catalyst.

Organic solvents which are preferably suitable are: aliphatic and aromatic hydrocarbons, such as, for example, benzene, toluene, xylene, petroleum ether and cyclohexanes; halogenated hydrocarbons, such as chlorobenzene, methylene chloride, chloroform and carbon tetrachloride; ethers, such as diethyl ether and diisopropyl ether; and their mixtures.

Strong bases which are preferably suitable are: alkali metal hydroxides, such as sodium hydroxide or potassium hydroxide, and also alkali metal carbonates or alkaline earth metal carbonates.

Phase transfer catalysts which are preferably suitable are: quaternary ammonium salts or ammonium hydroxides and phosphonium salts. Examples which may be mentioned are: tetra-n-butylammonium bromide, benzyltriethylammonium chloride, tetra-n-butylammonium hydroxide, benzyltrimethylammonium chloride, tributylhexadecylphosphonium bromide, ethyltriphenylphosphonium bromide, tetraphenylphosphonium chloride, benzyltriphenylphosphonium iodide or tetrabutylphosphonium chloride.

When carrying out process (b) according to the invention, the reaction temperatures can be varied within a substantial range. In general, the process is carried out between 10° C. and 50° C., preferably between 20° C. and 30° C.

When carrying out process (b) according to the invention, it is preferred to employ 1 to 3 mols of methylating agent per mol of the compound of the formula (Ia). The intermediates or end products of the formula (Ib) are isolated in a customary manner.

Suitable diluents for process (c) according to the invention are all inert organic solvents. These include hydrocarbons, such as toluene or xylene; chlorinated aromatic hydrocarbons, such as chlorobenzene, 1,2-dichlorobenzene or 1,2,4-trichlorobenzene; ethers, such as tetrahydrofuran or dioxane; alcohols, such as methanol, ethanol, propanol or isopropanol; amides, such as N,N-dimethylformamide or tetramethylurea, or sulphoxides, such as dimethyl sulphoxide. Isopropanol is preferably used in the reaction.

When carrying out process (c) according to the invention, the reaction temperatures can be varied within a substantial range. In general, the process is carried out at temperatures between 20° C. and 170° C., preferably at temperatures between 60° C. and 90° C.

In a particularly advantageous embodiment of process (c) according to the invention, the process is carried out in the presence of at least the equimolar amount of a lower aliphatic carboxylic acid. Acetic acid is preferably used for this purpose. This process permits operation with a relatively small excess of amine. In this embodiment, it is possible to increase the rate of the reaction by adding a catalytic amount of an organic sulphonic acid. p-Toluenesulphonic acid is preferably used for this purpose.

When carrying out process (c) according to the invention, it is expedient to employ 1 to 3 mols of a lower aliphatic carboxylic acid, and if appropriate 0.01 to 0.05 mol of an organic sulphonic acid, and 1 to 7 mols of amine of the formula (III) per mol of the 3-alkylthiotriazinones of the formula (Ia), and the mixture is heated until mercaptan is no longer eliminated and then worked up in a customary fashion.

The active compounds according to the invention can be used as defoliants, desiccants, agents for destroying broad-leaved plants and, especially, as weedkillers. By weeds, in the broadest sen be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the cenera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the cenera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the cenera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the cenera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields and for the selective combating of weeds in annual cultures. In this connection, the active substances of the formula (I) according to the invention can be employed with particularly good success for combating monocotyledon and dicotyledon weeds in monocotyledon and dicotyledon cultures, in particular in wheat, barley, corn, soy bears and cotton.

Moreover, the active compounds according to the invention engage in the metabolism of the plants and can therefore be employed as growth regulators.

Experience to date of the mode of action of plant growth regulators has shown that an active compound can also exert several different actions on plants. The actions of the compounds depend essentially on the point in time at which they are used, relative to the stage of development of the plant, and on the amounts of active compound applied to the plants or their environment and the way in which the compounds are applied. In each case, growth regulators are intended to influence the crop plants in the particular manner desired.

The amount of leaf on plants can be controlled, under the influence of growth regulators, so that defoliation of the plants at a desired point in time is achieved. Such defoliation is of great importance in the mechanical harvesting of cotton, but is also of interest for facilitating harvesting in other crops, such as, for example, in viticulture. Defoliation of the plants can also be carried out to lower the transpiration of plants before they are transplanted.

The active compounds can be converted into the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene, or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly-disperse silica, alumina and silicates; as solid carriers for granules there are suitable:

for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumin hydrolysis products; as dispersing agents there are suitable: for example lignin-sulphite waste liquors and methylcellulose.

Adhesives such as carboxymethylcellulose and natural and synthetic polymers in the form of powders, granules or latexes, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

When used as herbicides, the active compounds according to the invention, as such or in their formulations, can also be used as a mixture with known herbicides for controlling weeds, readymixes or tank mixes being possible.

Suitable herbicides for the mixtures are known herbicides, such as, for example, 1-amino-6-ethylthio-3-(2,2-dimethylpropyl)-1,3,5-triazine-2,4(1H,3H)-dione (AMETHYDIONE) or N-(2-benzothiazolyl)-N,N′-dimethylurea (METABENZTHIAZURON) for combating weeds in cereals; 4-amino-3-methyl-6-phenyl-1,2,4-triazin-5(4H)-one (METAMITRON) for combating weeds in sugar beet and 4-amino-6-(1,1-dimethylethyl)-3-methylthio-1,2,4-triazin-5(4H)-one (METRIBUZIN) for combating weeds in soy beans. Mixtures with 2,4-dichlorophenoxyacetic acid (2,4-D); 4-(2,4-dichlorophenoxy)-butyric acid (2,4-DB); 2,4-dichlorophenoxypropionic acid (2,4-DP); 5-(2-chloro-4-trifluoromethyl-phenoxy)-2-nitro-benzoic acid (ACIFLUORFEN); 2-chloro-2′,6′-diethyl-N-methoxy-methyl-acetanilide (ALACHLOR); methyl-6,6-dimethyl-2,4-dioxo-3-[1-(2-propenyloxyamino)-butylidene]-cyclohexanecarboxylic acid (ALLOXYDIM);2-chloro-4-ethylamino-6-isopropylamino-1,3,5-triazine (ATRAZINE); 3-isopropyl-2,1,3-benzo-thiadiazin-4-one 2,2-dioxide (BENTAZONE); methyl 5-(2,4-dichlorophenoxy)-2-nitrobenzoate (BIFENOX); 3,5-dibromo-4-hydroxy-benzonitrile (BROMOXYNIL); N-(butoxymethyl)-2 -chloro-N-(2,6-diethylphenyl)-acetamide(-BUTACHLOR);ethyl 2-{[(4-chloro-6-methoxy-2-pyrimidinyl)-aminocarbonyl]aminosulphonyl}-benzoate (CHLORIMURON); 2-chloro-N-{[(4-methoxy-6-methyl-1,3,5-triazin-2-yl)-amino]-carbonyl}benzenesulphonamide (CHLORSULFURON); N,N-dimethyl-N′-(3-chloro-4-methylphenyl)-urea(CHLORTOLURON); exo-1-methyl4-(1-methylethyl)-2-(2-methylphenyl-methoxy)-7-oxabicyclo-(2,2,1)-heptane (CINMETHYLIN); 3,6-dichloro-2-pyridinecarboxylic acid (CLOPYRALID); 2-chloro-4-ethylamino-6-(3-cyano-propylamino)-1,3,5-triazine (CYANAZINE); 2-[4-(2,4-dichlorophenoxy)-phenoxy]-propionic acid, its methyl ester or its ethyl ester (DICLOFOP); 2-[(2-chlorophenyl)-methyl]-4,4-dimethylisoxazolidin-3-one (DIMETHAZONE); S-ethyl N,N-di-n-propyl-thiocarbamidate (EPTAME); 4-amino-6-t-butyl-3-ethylthio-1,2,4-triazin-5(4H)-one (ETHIOZIN); 2-{4-[(6-chloro-2-benzoxazolyl)oxy]-phenoxy}-propanoic acid, its methyl ester or its ethyl ester (FENOXAPROP); 2-[4-(5-trifluoromethyl-2-pyridyloxy)-phenoxy]-propanoic acid or its butyl ester (FLUAZIFOP); N,N-dimethyl-N′-(3-trifluoromethylphenyl)urea (FLUOMETURON); [(4-amino-3,5-dichloro-6-fluoro-2-pyridinyl)-oxy]-acetic acid or its 1-methylheptyl ester (FLUROXYPYR); 5-(2-chloro-4-trifluoromethyl-phenoxy)-N-methylsulphonyl-2-nitrobenzamide (FOMESAFEN); 2-{4[(3-chloro-5-(trifluoromethyl)-2-pyridinyl)-oxy]-phenoxy}-propanoic acid or its ethyl ester (HALOXYFOP); 2-[5-methyl-5-(1-methylethyl)-4-oxo-2-imidazolin-2-yl]-3-quinolincarboxylic acid (IMAZAQUIN); 2-[4,5-dihydro-4-methyl-4-isopropyl-5-oxo-(1H)-imidazol-2-yl]-5 -ethylpyridin-3-carboxylic acid (IMAZETHAPYR); 3,5-diiodo-4-hydroxybenzonitrile (IOXYNIL); N,N-dimethyl-N,-(4-isopropylphenyl)-urea (ISOPROTURON); (2-ethoxy-1-methyl-2-oxoethyl 5-[2-chloro-4-(trifluoromethyl)-phenoxy]-2-nitrobenzoate (LACTOFEN); (2-methyl-4-chlorophenoxy)acetic acid (MCPA); (4-chloro-2-methylphenoxy)-propionic acid (MCPP); N-methyl-2-(1,3-benzothiazol-2-yloxy)acetanilide(MEFENACET);2-chloro-N-(2,6-dimethylphenyl)N-[(1H)-pyrazol-1-yl-methyl]-acetamide (METAZACHLOR); 2-ethyl-6-methyl-N-(1-methyl-2-methoxyethyl)-chloroacetanilide (METOLACHLOR); 2-{[[((4-methoxy-6-methyl1,3,5-triazin-2-yl)-amino)-carbonyl]-amino]-sulphonyl}-benzoic acid or its methyl ester (METSULFURON); 4-(di-n-propylamino)-3,5-dinitrobenzenesulphonamide (ORYZALIN); 2-chloro-4-trifluoromethylphenyl 3-ethoxy-4-nitro-phenyl ether (OXYFLUORFEN); N-(1-ethylpropyl)-3,4-dimethyl-2,6-dinitroaniline (PENDIMETHALIN); 0-(6-chloro-3-phenylpyridazin-4-yl) S-octyl thiocarbonate (PYRIDATE); ethyl 2-[4-(6-chloro-quinoxalin-2-yl-oxy)-phenoxy]-propionate (QUIZALOFOP-ETHYL); 2-[1-(ethoxamino)-butylidene]-5-(2-ethylthiopropyl)-1,3-cyclohexadione (SETHOXYDIM); 2-chloro-4,6-bis-(ethylamino)-1,3,5-triazine (SIMAZINE); 2,4-bis-[N-ethylamino]-6-methylthio-1,3,5-triazine (SIMETRYNE); 4-ethylamino-2-t-butylamino-6-methylthio-s-triazine (TERBUTRYNE); methyl 3-[[[[(4-methoxy-6-methyl1,3,5-triazin-2-yl)-amino]-carbonyl]-amino]-sulphonyl]thiophene-2-carboxylate (THIAMETURON); S-[(4-chlorophenyl)-methyl]-diethylcarbamothioate (THIOBENCARB); S-(2,3,3-trichloroallyl) diisopropylthiocarbamate (TRIALLATE) and 2,6-dinitro-4-trifluoromethyl-N,N-dipropylaniline (TRIFLURALIN) are also possible.

Mixtures with other known active compounds, such as fungicides, insecticides, acaricides, nematicides, bird repellents, plant nutrients and agents which improve the soil structure are also possible.

The active compounds can be used as such, in the form of their formulations or as the use forms prepared therefrom by further dilution, such as ready-to-use solutions, suspensions, emulsions, powders, pastes and granules. They are applied in a customary manner, for example by watering, spraying, atomizing or scattering.

The active compounds according to the invention can be applied either before or after emergence of the plants.

They can also be incorporated in the soil before sowing.

When used as herbicides, the amount of active compound can vary within a substantial range. Essentially, it depends on the nature of the desired effects. In general, the application rates are between 0.01 and 10 kg of active compound per hectare of soil area, preferably between 0.05 and 5 kg per ha.

When used as growth regulators, the active compounds according to the invention can also be present in the formulations as mixtures with other known active compounds, such as fungicides, insecticides, acaricides and herbicides, and in mixtures with fertilizers and other growth regulators.

In this connection, the active compounds can be used as such, in the form of their formulations or as the use forms prepared therefrom, such as ready-to-use solutions, emulsifiable concentrates, emulsions, foams, suspensions, wettable powders, pastes, soluble powders, dusting agents and granules. They are applied in the customary manner for example by watering, spraying, atomizing, scattering, dusting, foaming, brushing on and the like. Furthermore, it is possible to apply the active compounds by the ultra-low volume method or to inject the preparation of active compound or the active compound itself into the soil. It is also possible to treat the seeds of the plants.

When used as growth regulators, the application rates can likewise be varied within a substantial range. In general, 0.01 to 50 kg, preferably 0.05 to 10 kg, of active compound are used per hectare of soil area.

As far as the application time is concerned, the growth regulators are applied within a preferred period of time, the exact definition of which depends on the climatic and vegetative circumstances.

The preparation and the use of the active com-pounds according to the invention can be seen from the examples below.

PREPARATION EXAMPLES

EXAMPLE 1

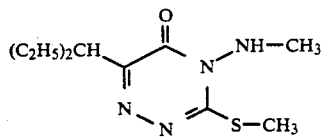
(Process b)

4.2 g (0.018 mol) of 4-amino-3-methylthio-6-(pent-3-yl)-1,2,4-triazin-5(4H)-one are introduced at room temperature into a mixture of 7.5 ml of 45% strength sodium hydroxide solution and 7.5 ml of toluene. 7.1 g (0.05 mol) of methyl iodide and 0.6 g of tetrabutylammonium bromide are then added all at once at room temperature. The mixture is stirred vigorously, and the temperature rises from 21° C. to 31° C. Stirring of the reaction mixture is continued for 1 hour, and the organic top phase is then removed in a separation funnel and stirred in 100 ml of water. The mixture is extracted with methylene chloride (three times, using 70 ml each time) and then filtered over silica gel, which, after concentrating, gives 3.8 g (87% of theory) of 4-methylamino-3-methylthio-6-(pent-3-yl)-1,2,4-triazin-5-(4H)-one as a colorless oil of refractive index $n_D^{20} = 1.553$.

Preparation of the starting material (a) 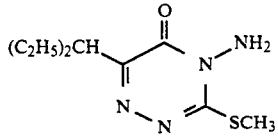 (Process a)

50 g (0.23 mol) of 4-amino-3-mercapto-6-(pent-3-yl)-1,2,4-triazin-5(4H)-one are dissolved in 260 ml of 1N sodium hydroxide solution, and the insoluble residue is filtered off. 36.9 g (0.26 mol) of methyl iodide are added at room temperature to the filtrate, and the mixture is stirred for 15 hours at this temperature. The solid which has precipitated is filtered off with suction, washed several times with water and dried in vacuum at room temperature.

Filtration in methylene chloride over silica gel gives 41.5 g (79% of theory) 4-amino-3-methylthio-6-(pent-3-yl)-1,2,4-triazin-5(4H)-one of melting point 50° C. to 56° C.

(b) 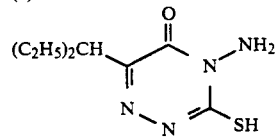

51.6 g (0.25 mol) of 3,3-diethyl-pyruvonitrile are stirred in 183.8 g of a 33% strength solution of bromine water in glacial acetic acid for 1 hour at 15° C. to 20° C.

After this, 4.5 g of water are added dropwise with stirring and ice-cooling in such a manner that the temperature of the reaction mixture does not exceed 20° C. Stirring of the mixture is continued for 1 hour at room temperature. A solution of 29.2 g (0.275 mol) of thiocarbohydrazide in 275 ml of 1N hydrochloric acid is then added dropwise with cooling at 15° C. to 20° C. When the addition is complete, stirring of the mixture is continued for 15 hours at room temperature. The crystalline product which has precipitated is filtered off with suction and washed with water until neutral.

Drying in vacuum at 50° C. gives 40.1 g (75% of theory) of 4-amino-3-mercapto-6-(pent-3-yl)-1,2,4-triazin-5(4H]-one of melting point 162° C. to 164° C.

(c) 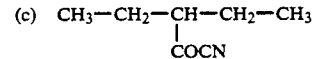

92.9 g (0.69 mol) of pentane-3-carboxylic acid chloride are heated to 120° C. 68.3 g (0.69 mol) of trimethylsilyl cyanide are added dropwise at this temperature within 2 hours. At a bath temperature of 120° C., stirring of the mixture is continued for 6 hours and the trimethylsylyl chloride which has formed is then distilled off under atmospheric pressure. The reaction product is fractionated via a 60 cm mirror-coated Vigreux column equipped with a rectifying head (reflux 5:1).

This gives 69.9 g (81% of theory) of 3,3-diethyl-pyruvonitrile of boiling point 48° C. to 56° C./20 mbar.

EXAMPLE 2

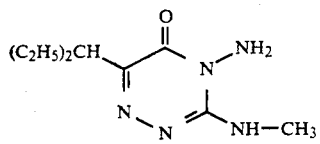
(Process c)

6.2 g (0.2 mol) of monomethylamine are introduced at 5° C. to 10° C. into the solution of 12 g (0.2 mol) of glacial acetic acid 150 ml of isopropanol. This reaction solution is then treated with 11.4 g (0.05 mol) of 4-amino-3-methylthio-6-(pent-3-yl)-1,2,4-triazin-5(4H)-one. The mixture is allowed to come to room temperature and is then refluxed for 24 hours. The reaction mixture is then concentrated, and the oily residue is stirred into water. The mixture is extracted using dichloromethane, and the extract is washed with water, dried over magnesium sulphate and concentrated. The residue is purified by silica gel filtration, using ethyl acetate.

This gives 6.8 g (64% of theory) of 4-amino-3-methylamino-6-(pent-3-yl)-1,2,4-triazin-5(4H)-one of melting point 119° C. to 120° C.

EXAMPLE 3

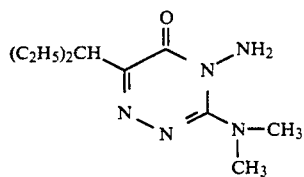
(Process c)

9.0 g (0.2 mol) of dimethylamine are passed at 5° C. to 10° C. into a solution of 12 g (0.2 mol) of glacial acetic acid in 150 ml of isopropanol. This reaction solution is then treated with 11.4 g (0.05 mol) of 4-amino-3-methylthio-6-(pent-3-yl)-1,2,4-triazin-5(4H)-one. The mixture is allowed to come to room temperature and is then refluxed for 24 hours. After this, the reaction mixture is concentrated and the residue is taken up in dichloromethane. The mixture is washed three times with water, dried over magnesium sulphate and concentrated. The oily residue is purified via silica gel column chromatography, using ethyl acetate as the eluent. This gives 8.1 g (72% of theory) of 4-amino-3-dimethylamino-6-(pent-3-yl)-1,2,4-triazin-5(4H)-one of refractive index $n_D^{20} = 1.545$.

The compound of the formula (I) which is listed in the table below is obtained in an analogous manner corresponding to the processes according to the invention:

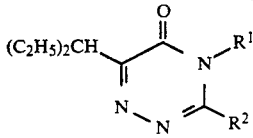
(I)

| Example No. | $R^1$ | $R^2$ | Physical Constant |
|---|---|---|---|
| 4 | —$NH_2$ | —$N(CH_3)C_2H_5$ | $n_D^{20} = 1.541$ |

USE EXAMPLES

In the Use Examples which follow, the compound listed below is employed as comparison substance:

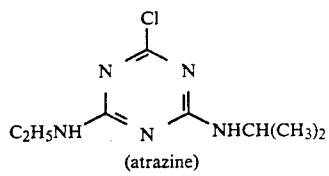
(A)

(atrazine)

(known from R. Wegler, Chemie de Pflanzenschutz- and Schadlingsbekampfungsmittel [Chemistry of Plant Protection Agents and Pesticides], Vol. 2, p. 368, Springer Verlag, 1970).

EXAMPLE A

| Pre-emergence test | |
|---|---|
| Solvent: | 5 parts by weight of acetone |
| Emulsifier: | 1 part by weight of alkylaryl polyglycol ether |

To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of active compound. It is expedient in this connection to keep constant the amount of water per unit area. The concentration of active compound in the preparation is of no importance, only the application rate of active compound per unit area being decisive. After three weeks, the degree of damage to the plants is rated in % damage in comparison to the development of the untreated control. The figures denote:

0% = no action (like untreated control)
100% = total destruction

A clearly superior effectiveness and selectivity towards crop plants, compared with the prior art, is shown in this test for example by the compounds of Preparation Examples 1, 3 and 4.

EXAMPLE B

| Post-emergence test | |
|---|---|
| Solvent: | 5 parts by weight of acetone |
| Emulsifier: | 1 part by weight of alkylaryl polyglycol ether |

To produce a suitable preparation of active compound, 1 part by weight of active compound is mixed with the stated amount of solvent, the stated amount of emulsifier is added and the concentrate is diluted with water to the desired concentration.

Test plants which have a height of 5-15 cm are sprayed with the preparation of the active compound in such a way as to apply the particular amounts of active compound desired per unit area. The concentration of the spray liquor is so chosen that the particular amounts of active compound desired are applied in 1,000 l of water/ha. After three weeks, the degree of damage to the plants is rated in % damage in comparison to the development of the untreated control. The figures denote:

0% = no action (like untreated control)
b 100% = total destruction

A clearly superior effectiveness and selectivity towards crop plants, compared with the prior art, is shown in this test for example by the compounds of Preparation Examples 2, 3 and 4.

EXAMPLE C

| Defoliation and desiccation of the leaves in cotton | |
| --- | --- |
| Solvent: | 30 parts by weight of dimethylformamide |
| Emulsifier: | 1 part by weight of polyoxyethylene sorbitan monolaurate |

To produce a suitable preparation of active compound, 1 part by weight of active compound is mixed with the stated amounts of solvent and emulsifier and the mixture is made up to the desired concentration with water.

Cotton plants are grown in a greenhouse until the 5th true leaf has unfolded completely. In this stage, the plants are sprayed with the preparations of active compound until dripping wet. After 1 week, the shedding of leaves and the desiccation of the leaves are rated, in comparison with the control plants.

A clear superiority compared with the untreated control is shown in this test for example by the compounds of Preparation Examples 2 and 3.

It is understood that the specification and examples are illustrative but not limitative of the present invention and that other embodiments within the spirit and scope of the invention will suggest themselves to those skilled in the art.

We claim:

1. A compound selected from the group consisting of
4-amino-3-methylamino-6-(pent-3-yl)-1,2,4-triazin-5(4H)-one,
4-amino-3-dimethylamino-6-(pent-3-yl)-1,2,4-triazin-5(4H)-one and
4-amino-3-ethylmethylamino-6-(pent-3-yl)-1,2,4-triazin-5(4H)-one.

2. A compound according to claim 1, wherein such compound is 4-amino-3-methylamino-6-(pent-3-yl)-1,2,4-triazin-5(4H)-one of the formula

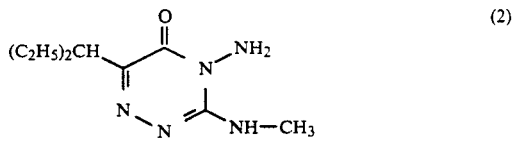

3. A compound according to claim 1, wherein such compound is 4-amino-3-dimethylamino-6-(pent-3-yl)-1,2,4-triazin-5(4H)-one of the formula

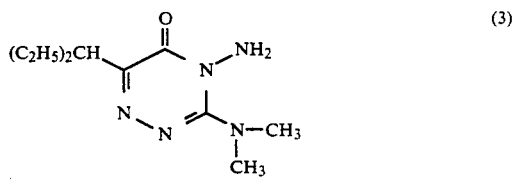

4. A compound according to claim 1, wherein such compound is 4-amino-3-ethylmethylamino-6-(pent-3-yl)-1,2,4-triazin-5(4H)-one of the formula

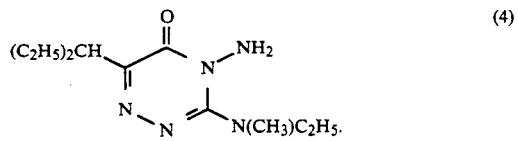

5. A herbicidal and plant growth-regulating composition comprising an amount effective therefor of a compound according to claim 1 and a diluent.

6. A method of regulating the growth of a plant or killing the plant which comprises applying to the plant or to a locus in which the plant is growing or to be grown a plant growth-regulating or herbicidally effective amount of a compound according to claim 1.

* * * * *